United States Patent [19]

Johnston

[11] 4,216,203

[45] Aug. 5, 1980

[54] PROCESS FOR PRODUCING INTERFERON

[75] Inventor: Michael D. Johnston, Beckenham, England

[73] Assignee: Burroughs Wellcome Co., Research Triangle Park, N.C.

[21] Appl. No.: 924,703

[22] Filed: Jul. 14, 1978

[30] Foreign Application Priority Data

Jul. 15, 1977 [GB] United Kingdom ............... 29871/77

[51] Int. Cl.² ............................................. A61K 45/02
[52] U.S. Cl. ..................................................... 424/85
[58] Field of Search ........................................... 424/85

[56] References Cited

FOREIGN PATENT DOCUMENTS 2282910 3/1976 France.

OTHER PUBLICATIONS

W. Rutter et al., Ann. Rev. Biochem, 42, 601–646 (1973).
F. N. Reizin et al., Antibiotiki (Moscow), 21 (1), pp. 45–48 (1976) English Translation.
R. Henneberry et al., Exp. Cell Reserach, 103, pp. 55–62 (1976).
R. Kameji et al., J. Biochem., 81, 1901 (1977).
P. Marks et al., Ann. Rev. Biochem., 47:419–448 (1978).
Strander et al., J. Clin, Mocrobiol. (1975), 1, 116–117.
Wright et al., J. of the Nat'l. Cancer Institute, (1974), 53, 1, 271–275, Interferon Production by Simian Lymphoblastoid cell lines.
Tovey et al., Nature, (1977), 267, 455–457.
Wright, Exp. Cell Res. (1973), 78, 456–460.
Deutsch et al., J. Cell Sci., (1976) 21, 391–406.
Simmons et al., J. Cell Biol. (1975), 66, 414–424.
Leder et al., Science (1975), 190, 893–894.
Ginsburg et al., Proc. Natl. Acad. Sci. USA (1973) 70, 2457–2461.

*Primary Examiner*—Nicholas S. Rizzo
*Assistant Examiner*—M. C. Eakin
*Attorney, Agent, or Firm*—Donald Brown

[57] ABSTRACT

Interferon is produced by incubating cells, which are susceptible to producing interferon, prior to induction by an inducer, in a medium containing an effective non-toxic amount of a straight chain, saturated carboxylic acid or a salt thereof.

6 Claims, No Drawings

PROCESS FOR PRODUCING INTERFERON

This invention relates to improvements in or relating to a process for producing the substances called interferons, which have non-specific antiviral effects.

An interferon is an antiviral proteinaceous substance which is produced by a cell in response to stimulation by a virus or other inducing agent. Interferons can be produced by most cells, for example white blood cells, fibroblasts, lymphoblastoid cells, cells of epithelial types such as kidney cells or HeLa cells, myeloma cells, etc. The particular cells chosen to produce interferon will depend on the product required, since interferons have characteristics depending on the host from which they are derived. If interferon is required for use in man, human cells are the preferred source. When formed, an interferon is excreted from the cell, and can then interact with other cells to inhibit virus replication or produce other effects. This antiviral effect is not specific to particular viruses, though some viruses are more sensitive to the effect of interferons than others.

Interferon has also been used in a chemotherapeutic regime for treatment of certain types of cancers, and appears to have a beneficial effect (Strander. H., Cantell, K., et al., Fogargty Intern. Center Proc., U.S. Govt. Printing Office, Washington D.C., 28: pp 377–381, 1977 Presented at the Conference at the National Institute of Health, Bethesda, Dec. 9–11, 1974.

Three main sources of considerable amounts of human interferon have been described, namely human peripheral blood leukocytes, human fibroblasts and human lymphoblastoid cells. However, it has so far been difficult to produce significant quantities of human interferon of a standard suitable for clinical use. For example, production of interferon from human peripheral leukocytes is limited by the availability of human blood. Large scale production of interferon from fibroblasts is hampered by the fact that these cells will only grow when adherent to a surface. Lymphoblastoid cells have the advantage that they can be grown in large suspension cultures, and can be induced to form interferon by treatment with a virus.

One of the processes which has been described for producing human lymphoblastiod interferon, involves the treatment of a cell suspension with a small amount of interferon from the homologous species with the intention of priming them for interferon production. This priming is followed by the addition of an inducer virus (see Strander, H., et al., J. Clin. Micro., 1, pp116–117 1975.

It has been found that the amounts of interferon produced from human lymphoblastoid cells by such methods can vary considerably, for example titres as high as 60–80 mega units (a mega unit equals $10^6$ units of interferon in terms of the Medical Research Council research standard preparation of interferon, 69/19, see N. Finter, Interferons, 1973, pp. 485–486, published by North Holland) of interferon per liter may be obtained, corrresponding to yields of 30-40 mega units per $10^9$ cells; on other occasions the titres may be only 1 mega unit or less per liter (or 0.5–0.7 mega units per $10^9$ cells) from similar cells induced under apparently identical conditions. The causes of such variations in the yield of interferon are unknown.

It has now been found that by treating cells, from which interferon is to be produced, with a carboxylic acid or salt thereof, and then inducing them to form interferon, relatively high yields of interferon are consistently produced.

According to the present invention there is provided a process for producing interferon which comprises adding an inducer to cells which are susceptible to being induced to form interferon characterized in that prior to induction the cells are incubated in a medium containing an effective, non-toxic amount of a straight chain, saturated carboxylic acid or a salt thereof.

The cells selected for interferon production are chosen according to requirement, thus if the interferon is for administration to humans, then human cells are the type usually selected. The cells used may be epithelial cells, or lymphoblastoid cells such as Namalva cells or other lymphoblastoid cell lines. Lines of lymphoblastoid cells that can be serially propagated in culture are readily derived from cultures of peripheral human blood leukocytes by well established methods (see for example, Hope, J. H., Horne, M. K., Scott, W., Int. J. Cancer, 3, pp 857–866 (1978), Hope, J. H., Horne, M. K., Scott, W., Int J. Cancer, 4, pp 255–260 (1969), Chang R. S., Golden H. D., Nature, 234, pp 359–360 (1971). Accordingly the leukocytes may be obtained from normal or diseased individuals, and they may be derived "spontaneously" if the cells are already infected with Epstein-Barr Virus (EBV), or they may be derived from cultures of leukocytes that are not infected with EBV, e.g. umbilical cord blood leukocytes, to which EBV or infectious mononucleosis or Burkitt lymphoma organisms have been added.

Lymphoblastoid cell lines are readily derived from the cells of patients with Burkitt's lymphoma as these are already infected with EBV. One particular line of Namalva was derived in Stockholm by Prof. G. Klein (nyornoi, O., Klein G., Adams, A., Dombon, L., Int. J. Cancer, 12, pp 396–408 (1973)) from cells obtained from an African female child of that name. Cells of this line have been found to produce large amounts of interferon when suitably stimulated (Strander, H., Morgensen, K. E., Cantell, K., J. Clin. Micro., 1, pp 116–117, (1975)). The subculture of this cell line was obtained from Dr. Ion Gresser (Villejuif, France) in January 1975. At that time the line was adapted to grow on medium RMPI 1640 with 10% foetal calf serum. In these laboratories the cells have been adapted to grow on the same medium supplemented with 5–7% serum derived from 6–8 month old calves and they have been subcultured two or three times a week during an 18 month period. A stock of these cells now termed Namalva/WRL has been laid down in a number of ampoules which are stored in liquid nitrogen. These cells have been shown to be free from mycoplasma infections and samples have been deposited with the American Type Culture Collection and assigned the designation ATCC No. CRL 1432.

Namalva/WRL cells were used in the examples described hereinafter but the invention also has been applied to other sub-lines of Namalva cells and other lymphoblastoid cells.

The carboxylic acid used in the medium preferably has from 2 to 8 carbon atoms, more preferably 3 to 6 carbon atoms, and most preferably it is butyric acid. If the acid itself is used, then on addition to the medium, which will contain various inorganic or organic salts, the salt of the acid is usually formed. Alternatively, it is possible to add the salt of the carboxylic acid to the medium in which case such salts as the sodium, potassium or ammonium salt may be used.

In order to produce interferon the selected cells must first be grown under conditions which are suitable and convenient for each cell type or strain as documented in the literature. For example, human lymphoblastoid cells, such as the Namalva cell line, grow readily in suspension in a growth medium, such as RPMI 1640 (Moore, G. E., et. al., 1967, *J. Amer. Med. Assoc.* 199, 519-524) supplemented with serum, for example calf or horse serum, usually at 5%-10% (v/v).

For producing interferon from lymphoblastoid cells, for example Namalva cells, the cells are grown in suspension until they have reached an adequate concentration, for example from 0.5 to $10 \times 10^6$ cells/ml, after which they can be conveniently processed for interferon production. For this purpose the cell concentration is adjusted to between 0.25 to $6 \times 10^6$ cells/ml, preferably 0.5 to $3 \times 10^6$ cells/ml, most preferably $1 \times 10^6$ cells/ml in a medium which can be one of the following: (a) fresh growth medium, (b) the spent growth medium in which the cells were previously grown, supplemented with fresh growth medium, or (c) the spent medium supplemented with fresh nutrients.

It is at this stage that the carboxylic acid or salt thereof may be added to the cell culture to give a final concentration of 0.1 to 10 mM, preferably 0.2 to 5 mM, most preferably 0.5 to 2.0 mM. The concentration is limited by the toxicity of the carboxylic acid for the cells but should be present in an amount so as to be effective in the enhancement of interferon production, and so the optimum balance between improved interferon yield and cell toxicity must be determined for the acid selected for use. Thus with carboxylic acids other than butyric acid, different molarities may be preferable. These cells are then incubated at from 33-38° C. preferably 35-37°C., for from 12 to 72 hours depending on the concentration of the carboxylic acid used, for example cells of the Namalva line of human lymphoblastoid cells are incubated for 48 hours with a final concentration of butyric acid of 1 mM, and at a pH of from 6.2 to 7.4, preferably 6.6 to 7.2.

After incubation the cells are then separated from the medium containing the carboxylic acid by some suitable method which does not damage them, for example centrifugation or filtration. The cells may, according to the known art (Tovey M. G., et.al.*Proc. of Soc. for Exp. Biol. & Med.,* 146, 809-815 (1974)) then be resuspended in a suitable medium, and induced to form interferon. For example they may be resuspended in medium RPM1 1640, containing no serum or supplemented with up to 5% v/v serum, to give a final cell concentration of from 0.25 to $8 \times 10^6$ cells/ml, preferably 0.5 to $4 \times 10^6$ cells/ml. A suitable inducer such as a virus, for example Sendai virus, is added to the cell suspension to give a final concentration of 5 to 200 HAU/ml, preferably 20 to 50 HAU/ml. After thorough mixing the cell suspension is incubated for a period of 12 to 48 hours at a temperature of from 34° to 37° C. For example at 35° C. the cell culture can conveniently be incubated overnight, during which time interferon is liberated from the cells into the medium. Following incubation the cells are removed by for example centrifugation, leaving a supernatant containing the crude interferon.

The advantage of incubating the cells in the presence of a straight chain carboxylic acid or salt thereof, before inducing them to form interferon, is that relatively high yields of interferon are produced, that is 5-50 mega units per liter or higher, more consistently than in the absence of the treatment. In addition, cells that have been adapted to grow in a medium containing a low serum supplement, eg. 1 to 2% v/v, will produce as much interferon as cells growing in medium supplemented with three to four times the amount of serum. This feature is of considerable importance since the cost of the serum comprises a large part of the cost of producing the interferon.

A further advantage of incubating the cells in the presence of a carboxylic acid, is that the step of priming the cells with a small amount of homologous interferon becomes redundant, resulting in a saving in production costs.

The invention will now be further described by way of the following examples which illustrate the invention but do not limit it in any way.

EXAMPLE 1

Human lymphoblastoid cells of the Namalva/WRL line were grown in suspension in a mechanically stirred 100 liter vessel in a growth medium consisting of medium RMPI 1640 supplemented with 7% calf serum, neomycin and polymyxin, and with bicarbonate for pH control. When the cells had reached a concentration of $2 \times 10^6$ cells per ml, 10 liters were withdrawn from the vessel and diluted with an equivalent volume of fresh growth medium. Butyric acid was added to give a final concentration of 1 mM, and the cells were incubated at 37° C. for 48 hours. During this period, the cells were stirred in glass flasks, and the ratio between the volume of cell suspension and the overlying air was approximately 2:5.

After this incubation period, the cells were centrifuged at 2,500 r.p.m. for 5 minutes at 20° C. in a MSE Coolspin centrifuge. The cell pellet was resuspended in medium RMPI 1640 containing 2% calf serum, and the cell concentration was estimated. The cells were diluted to a final concentration of $2.75 \times 10^6$ cells per ml, and to prime them, pre-formed lymphoblastoid interferon was added to give a final concentration of approximately 100 reference interferon units per ml. Sendai virus was then added to a final concentration of 75 haemagglutination units per ml. to induce interferon formation. After thorough mixing, the cell suspension was put into Thompson bottles (300 ml per bottle), which were incubated at 35° C. overnight. On the following day, the cell suspensions were centrifuged at 3,000 r.p.m. for 10 minutes at 4° C. in a Coolspin centrifuge. The supernatant fluid, containing the crude interferon, was acidified for 24 hours at pH 2, and then neutralised to pH 4 for subsequent storage.

Another portion of the cell suspension from the 100 liter vessel was handled in exactly the same way throughout except that no butyric acid was added.

Samples of the control cells and of the cells treated with butyric acid were assayed in parallel for their interferon content. The results obtained were:

Control cells : 3.75 log reference units of interferon/ml equivalent to 6 mega units/1.

Butyric acid treated cells : 4.80 log reference units of interferon/ml equivalent to 63 mega units/1.

EXAMPLE 2

Namalva/WRL cells were grown to a concentration of $2.5 \times 10^6$ cells/ml in the medium used in Example 1 and were collected by centrifugation at $800 \times g$ for 10 minutes; the cell pellet was resuspended in fresh growth medium. The cell suspension was diluted to a final concentration of $1.3 \times 10^6$ cells/ml, and 50 ml samples were dispensed into 75 cm² plastic tissue culture flasks. Different amounts of a 100 mM solution of sodium butyrate in phosphate buffered saline were then added to individual flasks to give a final concentration of sodium butyrate of 0, 0.1, 0.2, 0.5, 1, 2 and 5 mM. The flasks were incubated at 36° C. for 48 hours, and then the cells in each flask were concentrated by centrifugation at 800×g for 5 minutes. Each cell pellet was resuspended to a final concentration of 4.3×10⁶ cells/ml in RMPI 1640 medium containing 2% (v/v) calf serum (maintenance medium). Samples of 10 ml of each cell suspension were placed in two 25 cm² plastic tissue culture flasks, which were induced to form interferon by the addition of Sendai virus to give a final concentration of 40 HAU/ml.

The flasks were returned to 36° C. for 20 hours. The interferon produced by each culture was harvested by sedimenting the cells at 1,000×g for 5 minutes. The supernatant containing the interferon was adjusted to pH 2.0 by the addition of concentrated hydrochloric acid and stored at 4° C. overnight. On the following day, the pH was adjusted to 7.0, and each sample was assayed for its interferon content.

| Concentration of Sodium Butyrate used to pre-treat cells (mM) | Interferon titre ($\log_{10}$ reference interferon units/ml) | Interferon yield mega units per l. |
| --- | --- | --- |
| 0 | 4.09 | 12 |
| 0.1 | 4.05 | 11 |
| 0.2 | 4.26 | 18 |
| 0.5 | 4.62 | 42 |
| 1.0 | 4.92 | 83 |
| 2.0 | 4.96 | 91 |
| 5.0 | 4.70 | 50 |

EXAMPLE 3

The method of preparing interferon as described in Example 2 was followed except that the sodium butyrate was replaced by sodium acetate, and the concentrations used were 0, 0.2, 1.0, 5.0 mM. The results were as follows.

| Concentration of Sodium Acetate used to pre-treat cells (mM) | Interferon titre ($\log_{10}$ reference interferon units/ml) | Interferon yield mega units per l |
| --- | --- | --- |
| 0 | 3.55 | 3.5 |
| 0.2 | 3.52 | 3.3 |
| 1.0 | 3.59 | 3.9 |
| 5.0 | 3.98 | 9.6 |

EXAMPLE 4

The method of preparing interferon as described in Example 2 was followed except that sodium butyrate was replaced by sodium propionate, and the concentrations used were 0, 0.5, 1.0, 2.0, 5.0 and 10.0 mM. The results were as follows:

| Concentration of Sodium Proprionate used to pre-treat cells (mM) | Interferon titre ($\log_{10}$ reference interferon units/ml) | Interferon yield mega units/l |
| --- | --- | --- |
| 0 | 3.69 | 5 |
| 0.5 | 3.71 | 5 |
| 1.0 | 4.20 | 16 |
| 2.0 | 4.49 | 31 |
| 5.0 | 4.05 | 11 |
| 10.0 | 4.15 | 14 |

EXAMPLE 5

The method of preparing interferon as described in Example 2 was followed except that sodium butyrate was replaced by sodium pentanoate, and the concentrations used were 0, 0.2, 0.5, 1.0, 2.0, and 5.0 mM. The results were as follows:

| Concentration of Sodium Pentanoate used to pre-treat cells (mM) | Interferon titre ($\log_{10}$ reference interferon units/ml) | Interferon yield mega units/l |
| --- | --- | --- |
| 0 | 3.81 | 6 |
| 0.2 | 3.94 | 9 |
| 0.5 | 4.26 | 18 |
| 1.0 | 4.59 | 39 |
| 2.0 | 4.85 | 71 |
| 5.0 | 4.37 | 23 |

EXAMPLE 6

The method of preparing interferon as described in Example 2 was followed except that sodium butyrate was replaced by sodium hexanoate, and the concentrations used were 0, 0.2, 0.5, 1.0 and 2.0 mM. The results were as follows:

| Concentration of Sodium Hexanoate used to pre-treat cells (mM) | Interferon titre ($\log_{10}$ reference interferon units/ml) | Interferon yield mega units/l |
| --- | --- | --- |
| 0 | 3.20 | 2 |
| 0.2 | 3.69 | 5 |
| 0.5 | 3.63 | 4 |
| 1.0 | 3.80 | 6 |
| 2.0 | 3.99 | 10 |

EXAMPLE 7

Decay of the enhancement of interferon production resulting from sodium butyrate treatment of Namalva/WRL cells.

50 ml amounts of a suspension of Namalva/WRL cells having a concentration 1.0×10⁶ cells/ml in fresh RPMI 1640 medium containing 7% v/v calf serum were placed in 5 plastic tissue culture flasks having a surface area available for cell growth of 75 cm². Sodium butyrate in phosphate buffered saline was added to four of the flasks to a final concentration of 1 mM. The flasks were incubated at 36° for 48 hours. The cells in the flask which received no sodium butyrate and in one of the flasks which received 1 mM sodium butyrate were sedimented from the medium at 1000×g for 5 minutes, resuspended in RPMI 1640 medium containing 2% v/v calf serum and adjusted to 3.0×10⁶ cells/ml. They were induced to synthesize interferon by addition of Sendai virus to a final concentration of 20 HAU/ml. The cells in the remaining flasks were pooled, centrifuged at 1000×g for 5 minutes and resuspended to a concentration of $1.0 \times 10^6$ cells/ml in fresh RPMI 1640 growth medium containing no sodium butyrate. These cells were distributed in amounts of 50 ml into three new plastic tissue culture flasks of 75 cm² area and incubated at 36° C. On successive days the cells from one of these flasks were centrifuged at $1000 \times g$ for 5 minutes and resuspended in RPMI 1640 medium containing 2% v/v calf serum to $3.0 \times 10^6$ cells/ml and induced with Sendai virus as before.

| Butyrate conc. (mM) | Incubation days in presence of butyrate (days) | Subsequent incubation in absence of butyrate (days) | Interferon titre $\log_{10}$ units/ml | Interferon yield mega units/l |
| --- | --- | --- | --- | --- |
| 1. 0 | 0 | 0 | 4.05 | 11 |
| 2. 1 | 2 | 0 | 4.57 | 37 |
| 3. 1 | 2 | 1 | 4.30 | 20 |
| 4. 1 | 2 | 2 | 3.95 | 9 |
| 5. 1 | 2 | 3 | 3.92 | 8 |

EXAMPLE 8

Interferon production by vervet green monkey kidney cell line V3 cells treated with sodium butyrate.

Plastic tissue culture flasks having a surface area of 25 cm² available for cell growth were seeded with V3 cells, Christofinis G. J., *J. Med. Micro*, 3(2), 251–258, 1970, at $1.5 \times 10^5$ cells/ml in 10 ml of Eagles Basal medium containing 4% v/v of foetal calf serum. The flasks were placed at 36° C. for 24 hours to allow the cells to attach to the plastic and establish. The growth medium was removed from each flask and the cells re-fed with 10 ml of fresh growth medium. To one flask sodium butyrate in phosphate buffered saline was added to a final concentration of 2 mM. Both flasks were then incubated at 36° C. for 48 hours. The growth medium was removed and each culture was inoculated with 0.5 ml of Sendai virus at 2000 HAU/ml. The flasks were returned to 36° C. for 1 hour to allow the virus to attach to the cells. The inoculum was removed and the cell sheets were washed once with phosphate buffered saline and then re-fed with 10 ml of Eagles Basal medium containing 2% v/v foetal calf serum. The flasks were incubated at 36° C. for 24 hours after which the interferon in the supernatant medium was harvested. The interferon-containing medium was processed as usual at pH 2 and assayed.

|  |  | Interferon titre ($\log_{10}$ units/ml) | Interferon yield mega units/l |
| --- | --- | --- | --- |
| 1. | $V_3$ without sodium butyrate | 0.66 | 0.005 |
| 2. | $V_3$ with sodium butyrate | 1.32 | 0.021 |

EXAMPLE 9

Enhancement of interferon titres from sodium butyrate treated Namalva/WRL cells induced with different inducers Namalva/WRL cells were sedimented from spent growth medium and resuspended in fresh RPMI 1640 medium containing 7% v/v calf serum to a concentration of $1.38 \times 10^6$ cells/ml. 500 ml were placed in each of two 1 liter glass jars, and to one culture sodium butyrate in phosphate buffered saline was added to a final concentration of 1 mM. The cultures were stirred at 36° for 48 hours. The cells were recovered by centrifugation and resuspended in RPMI 1640 medium containing 2% v/v calf serum to a concentration of $5.0 \times 10^6$ cells/ml. Aliquots of 10 ml of these cell preparations were induced with the agents tested. The supernatants from the virus-induced cultures were processed as usual at pH 2 before being assayed for their interferon content.

|  |  | Amount | Cells pretreated with butyrate | Interferon titre $\log_{10}$ units/ml | Interferon yield mega units/l |
| --- | --- | --- | --- | --- | --- |
| 1. | Sendai virus | 40 HAU/ml | − | 3.71 | 5 |
| 2. | Sendai virus | 40 HAU/ml | + | 4.56 | 36 |
| 3. | Newcastle Disease Virus | 20 HAU/ml | − | 2.45 | 0.3 |
| 4. | Newcastle Disease Virus | 20 HAU/ml | + | 3.19 | 2 |
| 5. | Semliki Forest Virus | 10 pfu/cell | − | 0.72 | 0.005 |
| 6. | Semliki Forest Virus | 10 pfu/cell | + | 1.22 | 0.02 |
| 7. | Polyribosinic acid - polyribocytidylic acid complex: DEAE-dextran | 100μg | − | 0.92 | 0.008 |
| 8. | Polyribosinic acid - polyribocytidylic acid complex: DEAE-dextran | 100μg | + | 1.66 | 0.05 |

Polyribosinic acid - polyribocytidylic acid complex: was obtained from P-L Biochemicals Inc. Lot No. 447121.

EXAMPLE 10

Butyric acid enhancement of interferon yield from Namalva/WRL cells adapted to grow on medium containing a reduced serum level Namalva/WRL cells, which normally grow in medium RPMI 1640 containing 7% calf serum, were adapted to grow in medium containing only 2% calf serum. These cultures regularly yielded cell counts of $1.5–2.0 \times 10^6$/ml.

A sample was taken from each of two such cultures (with cell counts of 1.67 and $2.05 \times 10^6$/ml) and diluted ½ with fresh growth medium. Butyric acid was added to each at a final concentration of 1 mM and the two cultures stirred at 37° C. for 48 hours.

Subsequent to butyric acid treatment, the cells were induced to make interferon. Control inductions were also carried out using a further sample of cells from the two parent (non-butyric acid treated) cultures, which of course had been grown for a further two days in normal growth medium. The butyric acid treated and control cells were centrifuged and resuspended in fresh medium at a concentration of $2.75 \times 10^6$ cells per ml. Sendai virus, 50 HAU/ml, was added and the cultures incubated at 35° C. overnight.

Interferon titres from these cultures were:

Controls (no butyric acid): $Log_{10}$ 3.45 and 3.46/ml or 3 mega units/l.

B.A. treated cells: $Log_{10}$ 4.69 and 4.82/ml or average 58 mega units/l.

I claim:

1. A process for producing interferon which comprises adding an inducer to epithelial or lymphoblastoid cells which are susceptible to being induced to form interferon the improvement which comprises incubating the cells, prior to induction, in a medium containing an effective non-toxic amount of a straight chain, alkansic acid having from 2 to 6 carbon atoms, or a salt thereof.

2. A process according to claim 1 wherein said cells are lymphoblastoid cells.

3. A process according to claim 2 wherein said lymphoblastoid cells are Namalva cells.

4. A process according to claim 1 wherein said carboxylic acid is butyric acid.

5. A process according to any one of claims 1 to 3 and 4 wherein said acid, or salt thereof is added to said medium to give a final concentration of 0.1 to 10 mM.

6. A process according to any one of claims 1 to 3 and 4 wherein said acid, or salt thereof, is added to said medium to give a final concentration of 0.2 to 5 mM.

* * * * *